United States Patent
Hart et al.

[19]

[11] Patent Number: 5,876,395
[45] Date of Patent: Mar. 2, 1999

[54] ADJUSTABLE ATHLETIC SUPPORT GARMENT AND INCONTINENCE PAD HOLDER

[76] Inventors: James E. Hart; Linda W. Hart, both of 2465 Cajun Dr., Martietta, Ga. 30066

[21] Appl. No.: 919,672

[22] Filed: Aug. 28, 1997

[51] Int. Cl.$^6$ ...................................................... A61F 13/15
[52] U.S. Cl. .......................... 604/393; 604/394; 604/400; 604/402; 2/401; 450/100; 450/103
[58] Field of Search .................... 604/392–396, 604/400–402; 2/401, 402, 405, 406, 408; 450/100, 102, 103; 602/67, 70, 72, 73

[56] References Cited

U.S. PATENT DOCUMENTS

| Re. 21,092 | 5/1939 | Lankenau | 604/392 |
|---|---|---|---|
| 1,342,588 | 6/1920 | Higgins | 604/401 |
| 1,614,180 | 1/1927 | Bennet | 604/401 |
| 1,924,642 | 8/1933 | Frieman | 604/401 |
| 3,499,442 | 3/1970 | Steinmetz | 128/159 |
| 3,504,671 | 4/1970 | Nelkin | 128/158 |
| 3,547,117 | 12/1970 | Smithers | 128/158 |
| 3,882,870 | 5/1975 | Hathaway | 128/284 |
| 3,963,022 | 6/1976 | Rotello | 602/70 |
| 4,122,849 | 10/1978 | Dietz | 128/158 |
| 4,134,400 | 1/1979 | Matteo | 128/158 |
| 4,186,739 | 2/1980 | Hail | 128/158 |
| 4,378,010 | 3/1983 | McDonald . | |
| 4,453,541 | 6/1984 | Castelli . | |
| 4,526,167 | 7/1985 | Ebenal . | |
| 4,622,962 | 11/1986 | Kauffman . | |
| 4,679,554 | 7/1987 | Markham . | |
| 4,702,239 | 10/1987 | Ichikawa . | |
| 4,838,886 | 6/1989 | Kent | 604/392 |
| 4,932,950 | 6/1990 | Johnson | 604/402 |
| 5,003,972 | 4/1991 | Kestler . | |
| 5,012,802 | 5/1991 | Bischoff . | |
| 5,239,706 | 8/1993 | Stevenson | 604/396 |
| 5,407,438 | 4/1995 | Hedlund et al. | 604/385.2 |
| 5,651,779 | 7/1997 | Burrell | 604/402 |

*Primary Examiner*—Mark O. Polutta

[57] ABSTRACT

A reusable, adjustable athletic support garment designed for wear with an absorbent material, such as an incontinence pad. The invention includes an adjustable waistband (12), a front panel (14), a rear panel (16), adjustable front panel support straps (18) and adjustable rear panel support straps (20). An absorbent material, such as an incontinence pad, is worn within the front panel (14) or within the rear panel (16), or within both. Connected to the front panel (14) are the front panel support straps (18) which extend downward from the groin region, rearward between a wearer's legs, and upward to the waistband (12) to which they are adjustably fastened. Connected to the rear panel (16) are the rear panel support straps (20) which extend downward from the buttocks region, forward between the wearer's legs, and upward to the waistband (12) to which they are adjustably fastened.

14 Claims, 4 Drawing Sheets

ADJUSTABLE ATHLETIC SUPPORT GARMENT AND INCONTINENCE PAD HOLDER

FIELD OF THE INVENTION

This invention relates to an athletic support garment, specifically one which is adjustable and which is used with absorbent material, such as absorption pads, for bladder and bowel incontinence.

DESCRIPTION OF THE RELATED ART

Males and females who suffer from incontinence yet desire to lead active lifestyles require an incontinence aid. Presently, an absorbent material, such as an absorbent pad, worn inside an undergarment is an effective aid for providing relief from incontinence. However, due to the very nature of incontinence, an absorbent pad may become totally saturated before a wearer has an opportunity to replace the pad. When such an absorbent pad becomes saturated with urine or fecal matter, two unfortunate conditions result. (1) As the absorbent pad becomes soaked, it becomes heavy, thereby weakening the support provided by the undergarment and diminishing the effectiveness of the undergarment as an aid for relieving incontinence. (2) Urine and fecal matter contained in the soaked absorbent pad penetrates and soaks the undergarment resulting in chafing and exposure to infection of those areas of the wearer's skin which are in contact with the soaked undergarment. Also, because the structure of such an undergarment is usually fixed and not adjustable, it is uncomfortable and perhaps impossible to be worn by a wearer who is substantially bed-ridden or otherwise unable to bend and stretch the body into positions required to put on the undergarment.

In U.S. Pat. No. 4,679,554, an athletic supporter is disclosed comprising a waistband, leg straps and a genital-supporting pouch constructed of an elasticized fabric intended to provide moisture transfer from the fabric instead of allowing the fabric to retain moisture. A disadvantage of this design is that the waistband is continuous and therefore not adjustable for the comfort of a wearer. A further disadvantage of a continuous waistband which is not adjustable is that it is not easily usable by a wearer who is unable to bend sufficiently to step into the waistband when putting on the athletic supporter. Another disadvantage of this design is that the straps supporting the pouch are secured to the waistband in a permanent fashion and therefore do not allow the wearer to adjust the support straps to provide maximum comfort for the wearer and strong support for an absorbent material, such as a pad, worn inside the pouch to aid in bladder incontinence. A further disadvantage of this design is the absence of a rear panel with adjustable support straps to contain an absorbent material, such as a pad, to aid in bowel incontinence.

An athletic supporter is disclosed in U.S. Pat. No. 4,186,739 comprising a waistband which is reinforced with narrower elastic material to prevent "rolling" of the upper edge of the waistband and to increase the functionality and comfort of the garment. A disadvantage of this design is that the ends of the waistband are sewn together to form a continuous waistband instead of the ends being adjustably connected to one another and therefore adjustable for the comfort of a wearer. Another disadvantage of this design is that the support straps for the pouch are attached to the waistband in permanent fashion and therefore are not adjustable to provide maximum comfort for the wearer and strong support for an absorbent material, such as a pad, worn inside the pouch to aid in bladder incontinence. Still another disadvantage of this design is the absence of a rear panel with adjustable support straps to contain an absorbent material, such as a pad, to aid in bowel incontinence and to allow the wearer to adjust the comfort and the support of the rear panel.

In U.S. Pat. No. 3,963,022, an athletic supporter is disclosed comprising a single fabric panel and a single piece elastic waistband. A disadvantage of this design lies in the single fabric panel extending from the abdomen of a wearer, between the wearer's legs and terminating in the buttocks region of the wearer. When an absorbent material, such as a pad, is worn inside the front area of the single fabric panel as a bladder incontinence aid, the single fabric panel is not provided a means to confine urine saturation to the front area of the single fabric panel. Likewise, when an absorbent material, such as a pad, is worn inside the rear area of the single fabric panel as a bowel incontinence aid, the single fabric panel is not provided a means to confine fecal matter saturation to the rear area of the single fabric panel. The single fabric panel can become soaked with urine and/or fecal matter, thereby exposing all regions of the wearer's skin covered by the single fabric panel to chafing and infection. Another disadvantage is the absence of a means to adjust the front and rear areas of the single fabric panel to provide maximum comfort for the wearer and strong support for an absorbent pad contained within either or both the front and the rear areas of the single fabric panel.

In U.S. Pat. No. 4,453,541, an athletic supporter is disclosed including a waistband with a pair of leg straps attached at one end to the waistband and at the other end to an elastic mesh enclosure. A disadvantage of this design is that the leg straps are sewn to the waistband and to the elastic mesh enclosure and therefore do not provide a wearer the ability to adjust the comfort and the support of the elastic mesh enclosure. Another disadvantage of this design is the single piece waistband which does not allow the wearer to adjust the comfort of the waistband. Still another disadvantage of this design is the absence of a rear panel with adjustable support straps to contain an absorbent material, such as a pad, to aid in bowel incontinence and which allows the wearer to adjust the comfort and the support of the rear panel.

A pad holder is disclosed in U.S. Pat. No. 4,838,886 comprised of a stretchable, knitted, panty-type holder for disposable or reusable absorbent wound dressings or pads. A disadvantage of this design is that the front and rear areas of the pad holder are not separated, thereby allowing a soaked pad to fully saturate the entire pad holder causing all regions of a wearer's skin which contact the pad holder to be contaminated with urine and/or fecal matter, resulting in chafing and exposure to infection of the wearer's skin. Another disadvantage of this design is absence of support straps provided to a separate front area of the pad holder to provide the wearer the ability to adjust the comfort and the support of the front area of the pad holder. A further disadvantage is the absence of support straps provided to a separate rear area of the pad holder to provide the wearer the ability to adjust the comfort and the support of the rear area of the pad holder.

U.S. Pat. No. 3,882,870 discloses a diaper suitable for adult use to fit comfortably without bulk or pressure. A disadvantage of this design is that the diaper is not comprised of separate front and rear areas, thereby allowing all regions of a wearer's skin which are in contact with a soaked diaper to be contaminated with urine and fecal matter, resulting in chafing and exposure to infection of the wearer's skin. Another disadvantage of this design is the absence of adjustable support straps provided to a separate front area of the diaper to provide the wearer the ability to adjust the comfort and the support of the front area of the diaper. A further disadvantage is the absence of adjustable support straps provided to a separate rear area of the diaper to provide the wearer the ability to adjust the comfort and the support of the rear area of the diaper.

A casing for an absorbent article is disclosed in U.S. Pat. No. 5,407,438 comprising a front part, a rear part and a crotch part made of flexible casing material. A disadvantage of this design is the front part, rear part, and crotch part are continuous and are not separated to prevent urine saturation of the front part from penetrating the crotch part and the rear part. Likewise the design does not prevent fecal matter saturation of the rear part from penetrating the crotch part and the front part. This disadvantage allows all regions of a wearer's skin which contact the front part, the crotch part, and the rear part to be exposed to urine and fecal matter, resulting in chafing and exposure to infection of the wearer's skin. Another disadvantage of this design is the absence of adjustable support straps provided to the front part of the casing to allow the wearer to adjust the comfort and the support of the front part of the casing. A further disadvantage of this design is the absence of adjustable support straps provided to the rear part of the casing to allow the wearer to adjust the comfort and the support of the rear part of the casing.

SUMMARY OF THE INVENTION

Accordingly, several objects and advantages of our invention are:

(a) to provide an athletic support garment which includes a front panel capable of containing an absorbent material, such as an incontinence pad, to aid in bladder incontinence;

(b) to provide an athletic support garment which includes a rear panel capable of containing an absorbent material, such as an incontinence pad, to aid in bowel incontinence;

(c) to provide an athletic support garment which includes an adjustable waistband to provide a male or female wearer the ability to adjust the comfort of the waistband;

(d) to provide an athletic support garment which includes adjustable front panel support straps and adjustable rear panel support straps to provide independent support for the front panel and independent support for the rear panel and to allow the male or female wearer to adjust the comfort and support of the front panel and the rear panel;

(e) to provide an athletic support garment which, when used with an incontinence pad placed within the front panel, confines urine saturation to the front panel, thereby restricting urine contamination of the wearer's skin to the groin region;

(f) to provide an athletic support garment which, when used with an incontinence pad placed within the rear panel, confines fecal matter saturation to the rear panel, thereby restricting fecal matter contamination of the wearer's skin to the anal and buttocks region;

(g) to provide an athletic support garment which can be put on by the wearer without causing the wearer to stoop or bend;

Further objects and advantages are to provide an adjustable athletic support garment and incontinence pad holder which is washable and reusable, is simple to use, and is inexpensive to manufacture. Still further objects and advantages will become apparent from a consideration of the ensuing description and drawings.

SUMMARY

The purpose of the present invention is to provide a simply constructed, comfortable, strong, effective, washable, adjustable athletic support garment for wear with or without an absorbent material, such as an incontinence pad, worn within the front panel of the athletic support garment to aid in bladder incontinence and for wear with or without an absorbent material, such as an incontinence pad, worn within the rear panel of the athletic support garment to aid in bowel incontinence.

DESCRIPTION OF THE PREFERRED EMBODIMENTS

Figure 1:
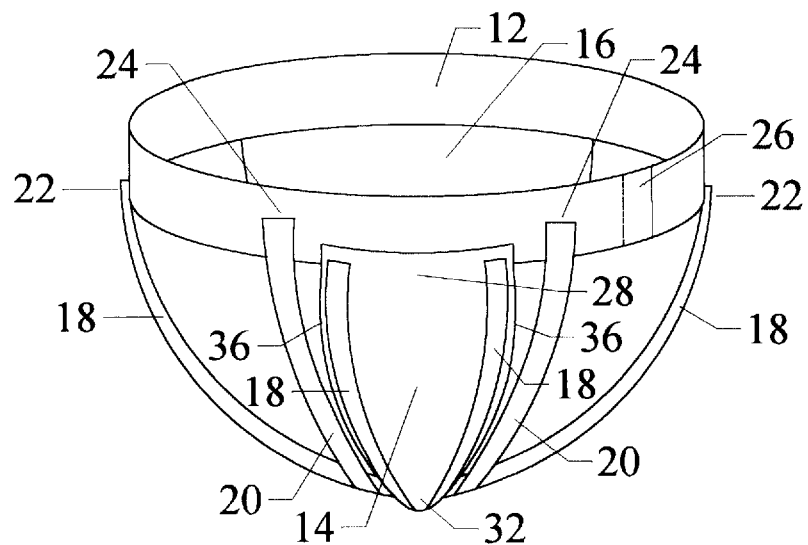
FIG. 1 shows a front perspective view of one embodiment of our invention.
Figure 2:
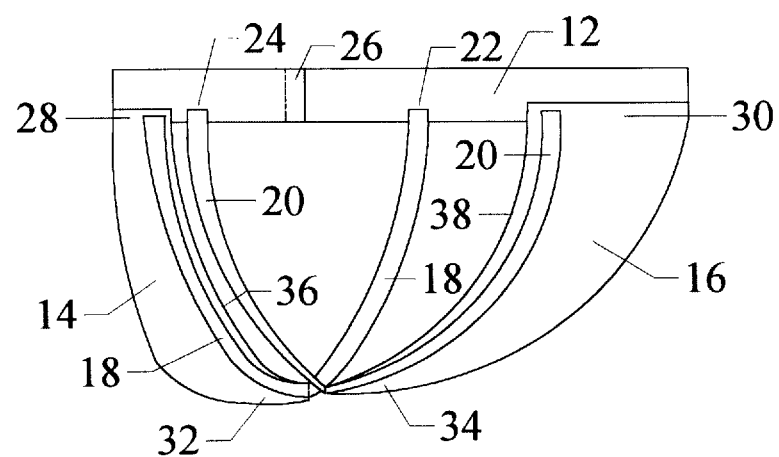
FIG. 2 shows a side planar view of the embodiment shown in FIG. 1.
Figure 3:
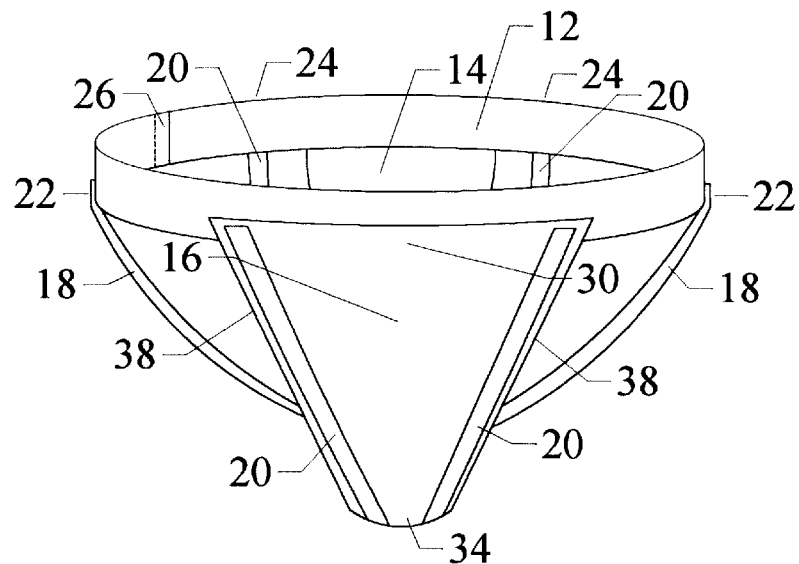
FIG. 3 shows a rear perspective view of the embodiment shown in FIG. 1.

In FIGS. 1 through 3 is shown a typical embodiment of an athletic support garment including an elastic waistband 12. The waistband 12 is constructed of a single length of wide elastic, the ends of which are not sewn together. Instead, the ends of waistband 12 have attached hook and loop fastener material or other adjustable fastening means 40 for attachment, one end to the other, at adjustable fastener location 26. Attached to the front center portion of waistband 12 by sewing at top of front panel 28 is front panel 14. Front panel 14 is made of a washable textile fabric, such as cotton. Attached and fastened by sewing along two front panel lateral edges 36 are elastic front panel support straps 18, which extend from top of front panel 28 down the front panel lateral edges 36 to bottom of front panel 32. Front panel support straps 18 continue to extend from bottom of front panel 32 rearward, outward, and then upward to waistband 12 and are adjustably fastened to waistband 12 at adjustable fastener location 22. Front panel support straps 18 are narrower than elastic waistband 12. The ends of front panel support straps 18 which adjustably fasten to waistband 12 at adjustable fastener location 22 are adjustably fastened by hook and loop fastener material or other adjustable fastening means 40.

Attached to the rear center portion of waistband 12 by sewing at top of rear panel 30 is rear panel 16. Rear panel 16 is made from a washable textile fabric, such as cotton. Attached and fastened by sewing along two rear panel lateral edges 38 are elastic rear panel support straps 20, which extend from top of rear panel 30 down the rear panel lateral edges 38 to bottom of rear panel 34. Rear panel support straps 20 continue to extend from bottom of rear panel 34 forward and upward to waistband 12 and are adjustably fastened to waistband 12 at adjustable fastener location 24. Rear panel support straps 20 are narrower than elastic waistband 12. The ends of rear panel support straps 20 which adjustably fasten to waistband 12 at adjustable fastener location 24 are adjustably fastened by hook and loop fastener material or other adjustable fastening means 40.

Figure 4:
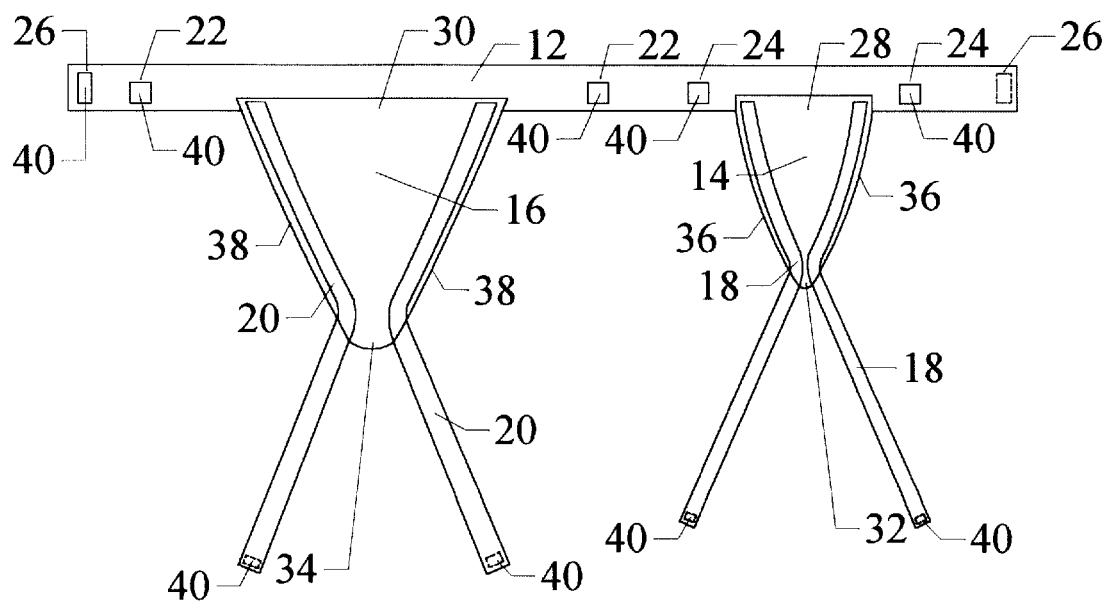
FIG. 4 shows a layout view of the embodiment shown in FIG. 1.

In FIG. 4, the typical embodiment is shown in layout view. Adjustable fastening means 40 are located on the ends of front panel support straps 18, on the ends of rear panel support straps 20, at adjustable fastener location 24 on waistband 12 adjacent to each end of top of front panel 28, at adjustable fastener location 22 on waistband 12 adjacent to each end of top of rear panel 30, and at adjustable fastener location 26 at both ends of waistband 12.

OPERATION—FIGS. 1 to 4

The manner of using the typical embodiment begins with placing the waistband 12 around the wearer's waist and adjustably fastening the two ends of waistband 12 at adjustable fastener location 26. Placing the waistband around the wearer's waste can be done with the wearer being in an upright position, either standing or seated, since the design of waistband 12 does not require the wearer to bend over and step into the waistband and then pull the waistband up to the waist. The waistband 12 can also be placed around the waist of a wearer in a lying position by placing the waistband in layout position, as shown in FIG. 4, and having the wearer roll the body over and onto the waistband 12.

Next, the front panel 14 is fastened into position by guiding the front panel support straps 18 rearward between the wearer's legs toward the wearer's buttocks. The front panel support straps 18 are then guided upward to the waistband 12 and adjustably fastened at adjustable fastener location 22.

The rear panel 16 is then fastened into position by guiding the rear panel support straps 20 forward between the wearer's legs toward front panel 14. The rear panel support straps 20 are then guided upward to the waistband 12 and adjustably fastened at adjustable fastener location 24.

Both the front panel support straps 18 and the rear panel support straps 20 are provided with sufficient adjustable fastening means (hook and loop fastener, adjustable snap fastener, or other adjustable fastening means) to allow the front panel 14 and the rear panel 16 to be adjusted to provide the desired degree of support and comfort for the wearer.

DESCRIPTION OF OTHER EMBODIMENTS AND RAMIFICATIONS

Figure 5:
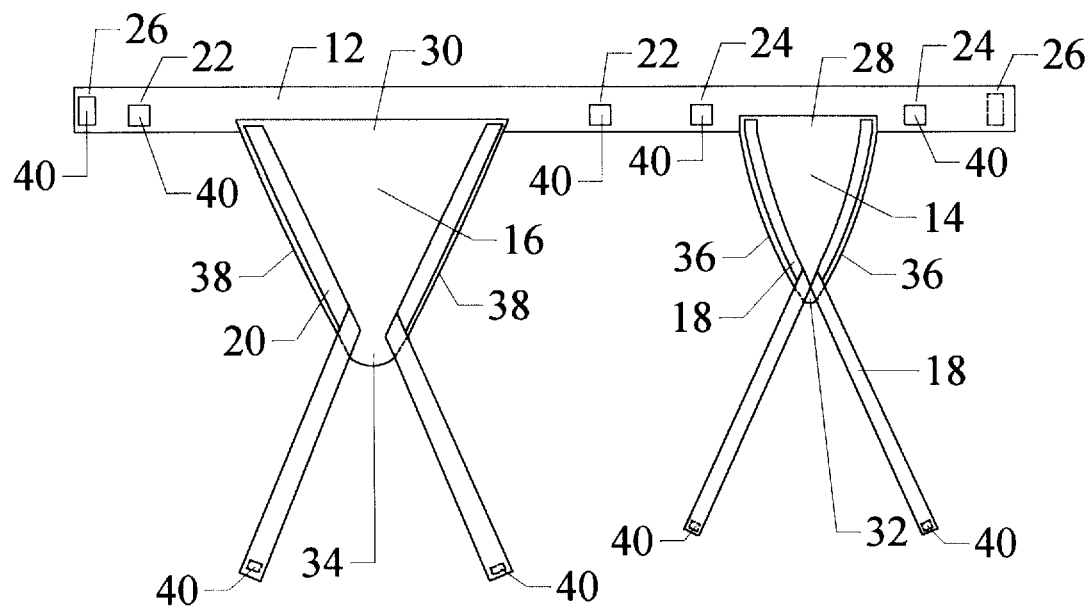
FIG. 5 shows a layout view of an embodiment with the front panel support straps and the rear panel support straps folded at the bottom of the front panel and at the bottom of the rear panel, respectively.

FIG. 5 shows another embodiment in which the elastic front panel support straps 18 are folded at an obtuse angle where they contact bottom of front panel 32. The rear panel support straps 20 are folded at bottom of rear panel 34 in the same manner. The purpose of the fold in front panel support straps 18 and rear panel support straps 20 is to exert tension on those portions of front panel support straps 18 and rear panel support straps 20 which are attached to front panel lateral edges 36 and rear panel lateral edges 38, respectively. This tension is to cause front panel 14 to spread outwardly to provide maximum coverage of the area intended to be covered and contained by front panel 14 and to cause rear panel 16 to spread outwardly to provide maximum coverage of the wearer's buttocks. This embodiment can apply to only front panel 14 or to only rear panel 16, or to both.

In another embodiment, front panel support straps 18 and rear panel support straps 20 are covered and encased within a portion of washable textile fabric, such as cotton. In FIGS. 1 to 4, this portion of fabric, covering and encasing front panel support straps 18, extends from bottom of front panel 32 to the ends of front panel support straps 18 where connection to waistband 12 occurs at adjustable fastener location 22. Again in FIGS. 1 to 4, this portion of fabric, covering and encasing rear panel support straps 20, extends from bottom of rear panel 34 to the ends of rear panel support straps 20 where connection to waistband 12 occurs at adjustable fastener location 24. Covering front panel support straps 18 and rear panel support straps 20 in such a manner will reduce irritation of sensitive skin and provide greater comfort to the wearer. This embodiment can apply to only front panel support straps 18 or to only rear panel support straps 20, or to both.

In another embodiment, waistband 12 in FIGS. 1 to 4 is covered and encased within a portion of washable textile fabric, such as cotton. Covering and encasing waistband 12 in such a manner will reduce irritation of sensitive skin and provide greater comfort to the wearer.

Figure 6:
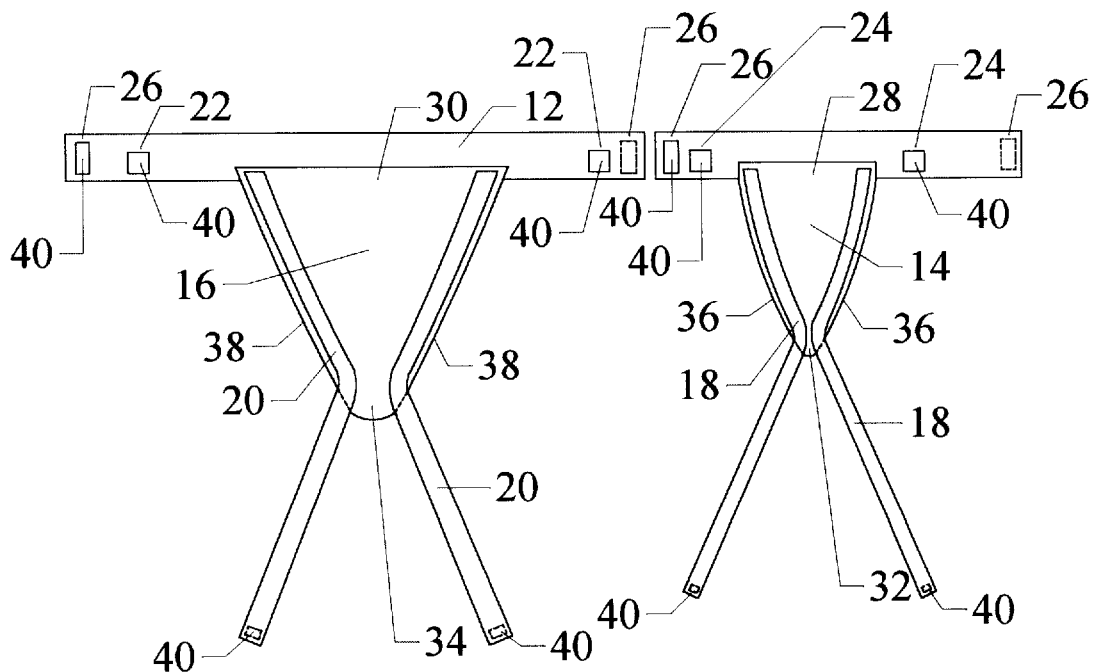
FIG. 6 shows a layout view of an embodiment with the waist band consisting of two portions.

FIG. 6 shows a layout view of another embodiment in which waistband 12 in FIGS. 1 to 4 consists of two lengths, connected by hook and loop fastener material or other adjustable fastening means. This embodiment provides the wearer another adjustment location on waistband 12 in addition to the adjustable fastening location 26 provided at the ends of waistband 12 in FIGS. 1 to 4.

Figure 7:
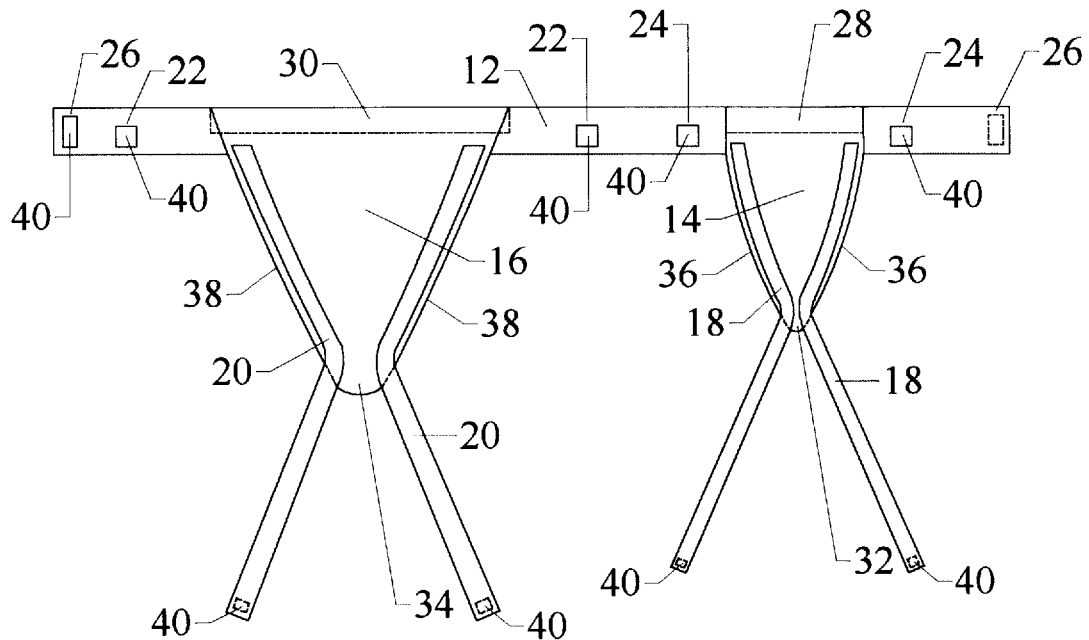
FIG. 7 shows a layout view of an embodiment with the front panel and the rear panel attached to the top inner surface of the waistband.

FIG. 7 shows another embodiment in which the top of front panel 28 is attached to the inner surface of waistband 12 by positioning front panel 14 onto waistband 12 with top of front panel 28 extending above top edge of waistband 12. Top of front panel 28 is then folded inward and down onto the inner surface of waistband 12 where it is attached to waistband 12 by sewing. In similar fashion, the top of rear panel 30 is attached to the inner surface of waistband 12 by positioning rear panel 16 onto waistband 12 with top of rear panel 30 extending above top edge of waistband 12. Top of rear panel 30 is then folded inward and down onto the inner surface of waistband 12 where it is attached to waistband 12 by sewing. This embodiment can apply to only front panel 14 or to only rear panel 16, or to both.

Figure 8:
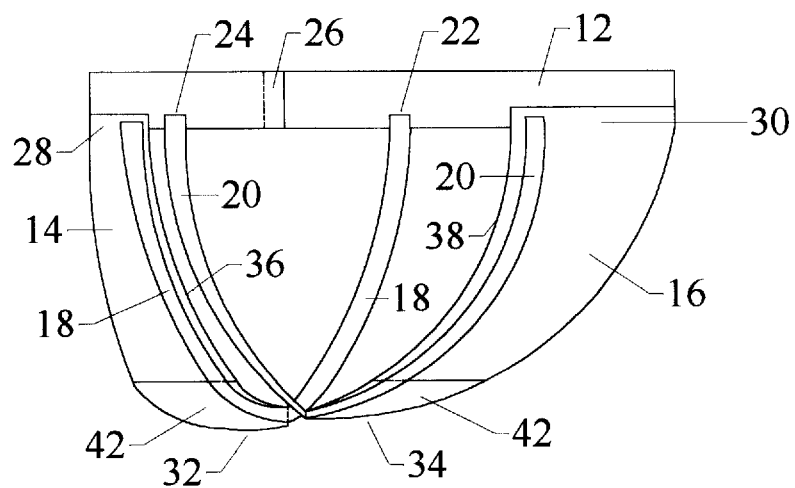
FIG. 8 shows a side planar view of an embodiment with a nonabsorbent material covering the bottom of the front panel and the bottom of the rear panel.

FIG. 8 shows another embodiment in which a portion of bottom of front panel 32 and a portion of bottom of rear panel 34 are provided a covering of nonabsorbent material 42, such as plastic, to enhance the confinement of urine saturation of an incontinence pad to front panel 14 and to enhance the confinement of fecal matter saturation of an incontinence pad to rear panel 16. This embodiment can apply to only front panel 14 or to only rear panel 16, or to both.

In another embodiment, front panel support straps 18 in FIGS. 1 to 4 begin at bottom of front panel 32 where they are attached by sewing. From bottom of front panel 32, front panel support straps 18 extend rearward, outward and upward to adjustable fastener locations 22 on waistband 12. Also in this embodiment, rear panel support straps 20 in FIGS. 1 to 4 begin at bottom of rear panel 34 where they are attached by sewing. From bottom of rear panel 34, rear panel support straps 20 extend forward and upward to adjustable fastener location 24 on waistband 12.

In another embodiment, front panel 14 and rear panel 16, shown in FIGS. 1 to 4, are constructed of a double layer of washable textile fabric instead of a single layer. The extra layer of fabric will provide greater support and comfort to the wearer. This embodiment can apply to only front panel 14 or to only rear panel 16, or to both.

In another embodiment, the ends of waistband 12, shown in FIGS. 1 to 4, are sewn together to form a continuous waistband.

In another embodiment, front panel 14 and rear panel 16 in FIGS. 1 to 4 are made of a stronger, more durable material, resulting in greater support for the wearer. This embodiment can apply to only front panel 14 or to only rear panel 16, or to both.

In another embodiment, top of front panel 28 and top of rear panel 30 in FIG. 4 are sewn at the top edge of waistband 12 instead of being sewn at the bottom edge of waistband 12 as shown in FIG. 4.

In another embodiment, top of front panel 28 and top of rear panel 30 in FIG. 4 are not sewn to waistband 12 but are adjustably fastened to waistband 12 with hook and loop fastener material or other adjustable fastening means to allow front panel 14 and rear panel 16 to be removed and reattached and to allow for additional adjustment of front panel 14 and of rear panel 16 by raising or lowering the fastening position of top of front panel 28 and by raising or lowering the fastening position of top of rear panel 30 on waistband 12. This embodiment can apply to only front panel 14 or to only rear panel 16, or to both.

In another embodiment, in FIG. 4 the portions of front panel support straps 18 attached and fastened along front panel lateral edges 36 are sewn into front panel 14 only at the top of front panel 28 and at the bottom of front panel 32. This results in the portions of front panel support straps 18 extending between top of front panel 28 and bottom of front panel 32 along front panel lateral edges 36 to stretch and contract freely without restriction. In this same embodiment, in FIG. 4 the portions of rear panel support straps 20 attached and fastened along rear panel lateral edges 38 are sewn into rear panel 16 only at the top of rear panel 30 and at the bottom of rear panel 34. Again this results in the portions of rear panel support straps 20 extending between top of rear panel 30 and bottom of rear panel 34 along rear panel lateral edges 38 to stretch and contract freely without restriction. In addition, this embodiment includes fastening the portions of front panel support straps 18 extending between top of front panel 28 and bottom of front panel 32 to front panel lateral edges 36 by sewing at other points between top of front panel 28 and bottom of front panel 32. This embodiment also includes fastening the portions of rear panel support straps 20 extending between top of rear panel 30 and bottom of rear panel 34 to rear panel lateral edges 38 by sewing at other points between top of rear panel 30 and bottom of rear panel 34. This embodiment can apply to only front panel 14 or to only rear panel 16, or to both.

In other embodiments, front panel 14 and rear panel 16 in FIGS. 1 to 4 are modified in any fashion necessary to provide a means of securing an absorbent material, such as an incontinence pad, in a stabilized position within front panel 14 and within rear panel 16. This embodiment can apply to only front panel 14 or to only rear panel 16, or to both.

In other embodiments, front panel 14 and rear panel 16 in FIGS. 1 to 4 are modified in any fashion necessary to provide a means of securing a cup or other protective shielding device in a stabilized position within front panel 14 and within rear panel 16. This embodiment can apply to only front panel 14 or to only rear panel 16, or to both.

CONCLUSION, RAMIFICATIONS, AND SCOPE

Accordingly, the reader will see that the combination adjustable athletic support garment and incontinence pad holder is an invention which can be worn with an absorbent material, such as an incontinence pad, placed within the front panel to aid in bladder incontinence. Likewise, it can be worn with an absorbent material, such as an incontinence pad, placed within the rear panel to aid in bowel incontinence. Furthermore, the invention has additional advantages including:

It is made of durable, washable, textile material, making it reusable, unlike incontinence garments which must be replaced after each use.

Both the front panel and the rear panel are adjustable, allowing a male or female wearer to enjoy constant, firm support for an incontinence pad worn within either the front panel or the rear panel, or within both.

The adjustable feature of both the front panel and the rear panel allow a wearer to adjust the comfort of the front panel and the rear panel whether wearing the invention with or without incontinence pads.

The front panel and the rear panel are separate from one another, thereby preventing bodily fluids contained within one panel from spreading to the other panel and unnecessarily exposing additional regions of a wearer's skin to chafing and possible infection.

The invention can be put on easily by a wearer, including a disabled wearer, from a seated or standing position without the discomfort of excessive bending or stooping.

Although the description above contains many specificities, these should not be construed as limiting the scope of the invention but as merely providing illustrations of some of the presently preferred embodiments of this invention. For example, the size of the rear panel could be narrower or wider. The size and shape of the front panel and the rear panel could be varied. The width of the front panel support straps and the rear panel support straps could be varied. The material used to construct any of the parts of the invention could be varied, etc.

Thus the scope of the invention should be determined by the appended claims and their legal equivalents, rather than by the examples given.

We claim:

1. A multipurpose, adjustable, athletic support garment for use with or without a urinary absorption device and for use with or without a fecal absorption device, comprising:

(a) a flexible waistband, said waistband having ends and said waistband having a front portion and a rear portion, (b) a means for adjustably connecting said ends of said waistband together in overlapping, parallel relationship, (c) a front panel of fabric adapted to be positioned in contact with the groin region of a wearer's body, said front panel having an upper portion, a lower portion, and lateral edges, (d) a means for attaching said upper portion of said front panel to said front portion of said waistband, (e) a pair of flexible front panel straps having front end portions, said front end portions being attached in parallel, overlying fashion to said lateral edges of said front panel, (f) said pair of flexible front panel straps adapted to be positioned between the wearer's legs and having rear end portions, said rear end portions being adjustably attached to said waistband, (g) a rear panel of fabric adapted to be positioned in contact with the buttocks and anal region of the wearer, said rear panel having an upper portion, a lower portion, and lateral edges, (h) a means for attaching said upper portion of said rear panel to said rear portion of said waistband, (i) a pair of flexible rear panel straps having rear end portions, said rear end portions being attached in parallel, overlying fashion to said lateral edges of said rear panel, (j) said pair of flexible rear panel straps adapted to be positioned between the wearer's legs and having front end portions, said front end portions being adjustably attached to said waistband, whereby said flexible front panel straps provide strong, independent support for said front panel and confine urine saturation within said front panel when an absorption device is worn within said front panel, and whereby said flexible rear panel straps provide strong, independent support for said rear panel and confine fecal saturation within said rear panel when an absorption device is worn within said rear panel.

2. The multipurpose, adjustable, athletic support garment of claim 1 wherein said ends of said waistband are securely fastened together to form a continuous waistband.

3. The multipurpose, adjustable, athletic support garment of claim 1 wherein said pair of flexible front panel straps and said pair of flexible rear panel straps are covered and encased within fabric.

4. The multipurpose, adjustable, athletic support garment of claim 1 wherein said front end portions of said pair of flexible front panel straps are attached to said lower portion of said front panel.

5. The multipurpose, adjustable athletic support garment of claim 1 wherein said rear end portions of said pair of flexible rear panel straps are attached to said lower portion of said rear panel.

6. The multipurpose, adjustable athletic support garment of claim 1 wherein said waistband is covered and encased within fabric.

7. The multipurpose, adjustable athletic support garment of claim 1 wherein said upper portion of said front panel is adjustably attached to said front portion of said waistband.

8. The multipurpose, adjustable athletic support garment of claim 1 wherein said upper portion of said rear panel is adjustably attached to said rear portion of said waistband.

9. The multipurpose, adjustable athletic support garment of claim 1 wherein said front panel is provided a means for securing an absorption device between said front panel and a wearer's body.

10. The multipurpose, adjustable athletic support garment of claim 1 wherein said rear panel is provided a means for securing an absorption device between said rear panel and a wearer's body.

11. The multipurpose, adjustable athletic support garment of claim 1 wherein said front panel is provided a means for securing a protective device between said front panel and a wearer's body.

12. The multipurpose, adjustable athletic support garment of claim 1 wherein said rear panel is provided a means for securing a protective device between said rear panel and a wearer's body.

13. The multipurpose, adjustable athletic support garment of claim 1 wherein said lower portion of said front panel is provided a moisture-proof layer of material attached to said lower portion of said front panel in overlying fashion, forming a barrier to confine urine saturation within said front panel.

14. The multipurpose, adjustable athletic support garment of claim 1 wherein said lower portion of said rear panel is provided a moisture-proof layer of material attached to said lower portion of said rear panel in overlying fashion, forming a barrier to confine fecal saturation within said rear panel.

* * * * *